(12) United States Patent
Kim (10) Patent No.: US 7,189,537 B2
(45) Date of Patent: Mar. 13, 2007

(54) HUMAN PROTOONCOGENE KG-20 AND PROTEIN ENCODED THEREIN

(76) Inventor: Jin Woo Kim, Hyundai Apt. 118-804, Apkujung-dong, Kangnam-ku, Seoul (KR) 135-110

( * ) Notice: Subject to any disclaimer, the term of this patent is extended or adjusted under 35 U.S.C. 154(b) by 244 days.

(21) Appl. No.: 10/486,401

(22) PCT Filed: Aug. 10, 2002

(86) PCT No.: PCT/KR02/01534

§ 371 (c)(1),
(2), (4) Date: Feb. 6, 2004

(87) PCT Pub. No.: WO03/016532

PCT Pub. Date: Feb. 27, 2003

(65) Prior Publication Data

US 2004/0175714 A1     Sep. 9, 2004

(30) Foreign Application Priority Data

Aug. 13, 2001   (KR) ............................... 2001-48733

(51) Int. Cl.
*C12P 21/02* (2006.01)
(52) U.S. Cl. ............. 435/69.1; 435/320.1; 435/252.33; 530/350; 536/23.5; 536/24.31
(58) Field of Classification Search .................... None
See application file for complete search history.

(56) References Cited

FOREIGN PATENT DOCUMENTS

WO         WO 01/27149 A1    4/2001

OTHER PUBLICATIONS

Asaumi et al., Genomics, vol. 58, 1999, pp. 293-301.*
Ausubel et al. (eds.), Short Protocols in Molecular Biology, Fourth Ed., 1999, pp. 16-1 to 16-17.*

* cited by examiner

*Primary Examiner*—James Ketter
(74) *Attorney, Agent, or Firm*—Anderson Kill & Olick, P.C.

(57) ABSTRACT

A human protooncogene having a base sequence of SEQ ID: 1 or a fragment thereof is overexpressed in various cancer tissues and can be used in diagnosing various cancers and an antisense gene complementary thereto can be used in treating cancers.

11 Claims, 5 Drawing Sheets

SEQUENCE LISTING

<160> NUMBER OF SEQ ID NOS: 2

<210> SEQ ID NO 1
<211> LENGTH: 622

```
<212> TYPE: DNA
<213> ORGANISM: Homo sapiens
<220> FEATURE:
<221> NAME/KEY: CDS
<222> LOCATION: (74)..(610)

<400> SEQUENCE: 1
ggcgcgggaa ttcgattgga tccggacaca ctttataatc tttccagttg atattgtcta      60
aagtcatgtc gac      atg act tta gac aat atc aac ctg gca gct gtg       106
                   Met Thr Leu Asp Asn Ile Asn Leu Ala Ala Val
                     1               5                  10 gat cga ata atc cgg gtg gat cat gca ggc gaa tat gga gca aac cgc       154
Asp Arg Ile Ile Arg Val Asp His Ala Gly Glu Tyr Gly Ala Asn Arg
         15                  20                  25 atc tat gcc ggg cag atg gct gtc ctg ggt cgg acc agc gtc ggg cca       202
Ile Tyr Ala Gly Gln Met Ala Val Leu Gly Arg Thr Ser Val Gly Pro
     30                  35                  40 gtc att cag aaa atg tgg gat caa gaa aag gac cat ttg aaa aag ttc       250
Val Ile Gln Lys Met Trp Asp Gln Glu Lys Asp His Leu Lys Lys Phe
 45                  50                  55 aat gag ttg atg gtt atg ttc agg gtc cgg cca aca gtt ctg atg ccc       298
Asn Glu Leu Met Val Met Phe Arg Val Arg Pro Thr Val Leu Met Pro
 60                  65                  70                  75 ttg tgg aac gtg ctg ggg ttt gca ctg ggg gcg ggg acc gcc ttg ctc       346
Leu Trp Asn Val Leu Gly Phe Ala Leu Gly Ala Gly Thr Ala Leu Leu
                 80                  85                  90 ggg aag gaa ggt gcc atg gcc tgc acc gtg gcg gtg gaa gag agc ata       394
Gly Lys Glu Gly Ala Met Ala Cys Thr Val Ala Val Glu Glu Ser Ile
             95                 100                 105 gca cat cac tac aac aac cag atc agg acg ctg atg gag gag gac cct       442
Ala His His Tyr Asn Asn Gln Ile Arg Thr Leu Met Glu Glu Asp Pro
        110                 115                 120 gaa aaa tac gag gaa ctt ctt cag ctg ata aag aaa ttt cgg gat gaa       490
Glu Lys Tyr Glu Glu Leu Leu Gln Leu Ile Lys Lys Phe Arg Asp Glu
    125                 130                 135 gag ctt gag cac cat gac ata ggc ctc gac cat gat gca gaa ttg gct       538
Glu Leu Glu His His Asp Ile Gly Leu Asp His Asp Ala Glu Leu Ala
140                 145                 150                 155 cca gcc tat gcc gtc ctg aag agc att atc cag gcc gga tgc aga gtg       586
Pro Ala Tyr Ala Val Leu Lys Ser Ile Ile Gln Ala Gly Cys Arg Val
                160                 165                 170 gcg ata tat tta tca gaa aga tta  taaagtgtgt cc                        622
Ala Ile Tyr Leu Ser Glu Arg Leu
                175

<210> SEQ ID NO 2
<211> LENGTH: 179
<212> TYPE: PRT
<213> ORGANISM: Homo sapiens

<400> SEQUENCE: 2

Met Thr Leu Asp Asn Ile Asn Leu Ala Ala Val Asp Arg Ile Ile Arg
 1               5                  10                  15

Val Asp His Ala Gly Glu Tyr Gly Ala Asn Arg Ile Tyr Ala Gly Gln
             20                  25                  30

Met Ala Val Leu Gly Arg Thr Ser Val Gly Pro Val Ile Gln Lys Met
         35                  40                  45

Trp Asp Gln Glu Lys Asp His Leu Lys Lys Phe Asn Glu Leu Met Val
     50                  55                  60

Met Phe Arg Val Arg Pro Thr Val Leu Met Pro Leu Trp Asn Val Leu
```

-continued

```
         65                  70                  75                  80
Gly Phe Ala Leu Gly Ala Gly Thr Ala Leu Leu Gly Lys Glu Gly Ala
                85                  90                  95

Met Ala Cys Thr Val Ala Val Glu Glu Ser Ile Ala His His Tyr Asn
                100                 105                 110

Asn Gln Ile Arg Thr Leu Met Glu Glu Asp Pro Glu Lys Tyr Glu Glu
            115                 120                 125

Leu Leu Gln Leu Ile Lys Lys Phe Arg Asp Glu Glu Leu Glu His His
        130                 135                 140

Asp Ile Gly Leu Asp His Asp Ala Glu Leu Ala Pro Ala Tyr Ala Val
145                 150                 155                 160

Leu Lys Ser Ile Ile Gln Ala Gly Cys Arg Val Ala Ile Tyr Leu Ser
                165                 170                 175

Glu Arg Leu
```

HUMAN PROTOONCOGENE KG-20 AND PROTEIN ENCODED THEREIN

FIELD OF THE INVENTION

The present invention relates to a novel protooncogene and protein encoded therein, which can be used in diagnosis of various cancers, preparation of transgenic animal, antisense gene therapy and anticancer drug development.

BACKGROUND OF THE INVENTION

Higher animals including man each carry approximately 100,000 genes, but only about 15% thereof is expressed, and characteristics of individual's biological processes, e.g., genesis, differentiation, homeostasis, responses to stimuli, control of cell division cycle, aging and apoptosis (programmed cell death), are determined depending on which genes are expressed (Liang, P. and A. B. Pardee, *Science* 257: 967–971, 1992).

Pathogenic phenomena such as tumorigenesis are caused by gene mutation which brings about changes in the mode of gene expression. Therefore, comparative studies of gene expressions in various cells have been conducted to provide bases for establishing viable approaches to the understanding of diverse biological phenomena.

It has been reported that tumorigenesis is caused by various genetic changes such as the loss of chromosomal heterozygosity, activation of oncogenes and inactivation of tumor suppressor genes, e.g., p53 gene (Bishop, J. M., *Cell* 64: 235–248, 1991; and Hunter, T., *Cell* 64: 249–270, 1991). Further, it has been reported that 10 to 30% of human cancer arises from the activation of oncogene through amplification of protooncogenes.

Therefore, the activation of protooncogenes plays an important role in the etiology of many tumors and there has existed a need to identify protooncogenes.

The present inventors have endeavored to unravel the mechanism involved in the tumorigenesis of cervical cancer; and, have unexpectedly found that novel protooncogenes, human cervical cancer proto-oncogene 1 (HCCR-1) (Korea Patent Application No. 2000-16757 (Mar. 31, 2000)) and HCCR-2 (Korea Patent Application No. 2000-71202 (Nov. 28, 2000)), are specifically overexpressed in cancer cells. Protooncogene causes quantitative and qualitative changes of the corresponding protein product expression via a conformational change (Weinberg, R. A., *Cancer Research* 49:3713–3721, 1989). The conformationally changed-cancer protein destroys signal transduction pathways in the cell surface, cytoplasm or nucleus; while in the absence of tumor suppressor gene product, it stimulates cell proliferation together with other cancer proteins, disturbs cell cycle, and destroys cell death (apoptosis) mechanism (Todd, R., *Anticancer Research* 19:4729–4746, 2000).

The yeast two-hybrid method, developed in 1989 by Fields et al. (Fields, S. and Song, O., *Nature* 340:245–246, 1989) for examining such protein-protein interactions, has been widely applied to elucidate the cell death mechanism (Wallach, D. et al., *Curr. Opin. Immunol.* 10:131–136, 1989) as well as other biological processes using various genetic tools (Pandey, A. and Mann, M., *Nature* 405:837–846, 2000).

In the course of screening for a novel binding protein to protooncogene KG-19 using the yeast two-hybrid method, the present inventors have discovered a novel human protooncogene, KG-20 which expresses a protein that specifically binds to protooncogene KG-19. Protooncogene KG-20 can be advantageously used in diagnosis, prevention and treatment of various cancers, e.g., leukemia, lymphoma, colon, breast, kidney, stomach, lung, ovary and uterine cancers.

SUMMARY OF THE INVENTION

Accordingly, an object of the present invention is to provide a novel protooncogene and a fragment thereof.

Other objects of the present invention are to provide:

a recombinant vector containing said protooncogene or a fragment thereof and a microorganism transformed therewith;

a protein encoded in said protooncogene and a fragment thereof;

a kit for diagnosing cancer which comprising said protooncogene or a fragment thereof;

a kit for diagnosing cancer which comprising said protein or a fragment thereof;

an antisense gene having a base sequence complementary to that of said protooncogene or a fragment thereof;

a process for treating or preventing cancer by using said antisense gene; and a process for screening anticancer drug candidates by using said protooncogene or a fragment thereof.

In accordance with one aspect of the present invention, there is provided a novel protooncogene having the nucleotide sequence of SEQ ID NO: 1 or a fragment thereof.

In accordance with another aspect of the present invention, there is provided a recombinant vector containing said protooncogene or a fragment thereof and a microorganism transformed with said vector.

In accordance with still another aspect of the present invention, there is provided a protein having the amino acid sequence of SEQ ID NO: 2 or a fragment thereof derived from said protooncogene or a fragment thereof.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

The novel protooncogene of the present invention, designated KG-20, consists of 622 base pairs and has the DNA sequence of SEQ ID NO: 1. This KG-20 protooncogene specifically binds to human protooncogene KG-19 (hereinafter "KG-19") described in Korea Patent Laid-open Publication No. 2002-41553.

In SEQ ID NO: 1, the open reading frame corresponding to base Nos. 74 to 613 is a full-length protein encoding region and the predicted amino acid sequence derived therefrom is shown in SEQ ID NO: 2, which consists of 179 amino acids ("KG-20 protein"). However, in consideration of the degeneracies of codons and the preferred codons in a specific animal wherein the protooncogene of the present invention is to be expressed, various changes and modifications of the DNA sequence of SEQ ID NO: 1 may be made, e.g., in the coding area thereof without adversely altering the amino acid sequence of the expressed protein, or in the non-coding area without adversely affecting the expression of the protooncogene. Therefore, the present invention also includes, in its scope, a polynucleotide having substantially the same base sequence as the inventive protooncogene, and a fragment thereof. As used herein, "substantially the same polynucleotide" refers to a polynucleotide whose base sequence shows 80% or more, preferably 90% or more, most preferably 95% or more homology to the protooncogene of the present invention.

The protein expressed from the protooncogene of the present invention consists of 179 amino acids and has the amino acid sequence of SEQ ID NO: 2. The molecular weight of this protein is about 20 kDa. The protooncogene KG-20 of the present invention is different from the *Homo sapiens* timing protein, CLK-1 (Vajo, Z. et al., *Am. J. Hum. Genet.* 61: A263-A263, 1997), in that the arginine residues at $34^{th}$ and $134^{th}$ position of CLK-1 are replaced with alanine and lycine, respectively, in SEQ ID NO: 2.

However, various substitution, addition and/or deletion of the amino acid residues of protein may be performed without adversely affecting the protein's function. Further, a portion of the protein may be used when a specific purpose is to be fulfilled. These modified amino acids and fragments thereof are also included in the scope of the present invention. Therefore, the present invention includes, in its scope, a polypeptide having substantially the same amino acid sequence as the protein derived from the oncogene of the present invention and a fragment thereof. As used herein, "substantially the same polypeptide" refers to a polypeptide whose amino acid sequence shows 80% or more, preferably 90% or more, most preferably 95% or more homology to the amino acid sequence of SEQ ID NO: 2.

The protooncogene, or the protein, of the present invention can be obtained from human placenta tissues or synthesized using a conventional DNA or peptide synthesis method. Further, the gene thus prepared may be inserted to a conventional vector to obtain an expression vector, which may, in turn, be introduced into a suitable host, e.g., a microorganism such as an *E. coli* or yeast, or an animal cell such as a mouse or human cell. A transformed cell with protooncogene KG-20 is designated "KG-20 cell".

A transformed host may then be used in producing the inventive DNA or protein on a large scale. For example, *E. coli* DH5α is transformed with expression vector pCEV-LAC (Miki, T. et al., *Gene* 83: 137–146, 1989) containing the inventive KG-20 gene to obtain an *E. coli* transformant designated DH5α/KG-20/pCEV-LAC which was deposited on Jun. 2, 2001 with the Korean Collection for Type Cultures (KCTC) (Address: Korea Research Institute of Bioscience and Biotechnology (KRIBB), #52, Oun-dong, Yusong-ku, Taejon, 305–333, Republic of Korea) under the accession number KCTC 1028BP, in accordance with the terms of Budapest Treaty on the International Recognition of the Deposit of Microorganism for the Purpose of Patent Procedure.

In preparing a vector, expression-control sequences, e.g., promoter, terminator, self-replication sequence and secretion signal, are suitably selected and combined depending on the host cell used.

The overexpression of the protooncogene of the present invention occurs in cancer tissues, e.g., leukemia, lymphoma, kidney, lung, stomach and skin cancer cell lines, suggesting that the inventive protooncogene induces such cancers. Further, when a normal human embryonic kidney (HEK) 293 cell is transfected with the protooncogene of the present invention, an abnormal cell is produced. Morphological characterizations with optical and electronic microscopes show that the abnormal cell has the form of a tumor cell. By using the hematoxylin-eosin dye method, it can be confirmed that the tumor cell is cancerous (carcinoma).

When normal HEK 293 cells are transfected with the protooncogene of the present invention and injected into the back of nude mice, tumorigenesis is observed after about 21 days from the injection, the tumor size becoming 2.0 cm×2.0 cm in 35 days.

Therefore, the protooncogene of the present invention is believed to be a factor common to all forms of cancers, and it can be advantageously used in the diagnosis of various cancers and the production of a transgenic animal as well as in an antisense gene therapy and anticancer drug development.

A diagnostic method that can be performed using the protooncogene of the present invention may comprise, for example, the steps of hybridizing nucleic acids separated from the body fluid of a subject with a probe containing the protooncogene of the present invention or a fragment thereof, and determining whether the subject has the protooncogene by using a conventional detection method in the art. The presence of the protooncogene may be easily detected by labeling the probe with a radioisotope or an enzyme. Therefore, a cancer diagnostic kit containing the protooncogene of the present invention or a fragment thereof is also included in the scope of the present invention.

A transgenic animal produced by introducing the protooncogene of the present invention into a mammal, e.g., a rat, is also included in the scope of the present invention. In producing such a transgenic animal, it is preferred to introduce the inventive protooncogene to a fertilized egg of an animal before the 8th cell cycle stage. The transgenic animal can be advantageously used in screening for carcinogens or anticancer agents such as antioxidants.

The present invention also provides an antisense gene which is useful in a gene therapy. As used herein, the term "an antisense gene" means a polynucleotide comprising a base sequence which is fully or partially complementary to the sequence of the mRNA which is transcribed from the protooncogene having the base sequence of SEQ ID NO: 1 or a fragment thereof, said nucleotide being capable of preventing the expression of the open reading frame (ORF) of the protooncogene by way of attaching itself to the protein-binding site of mRNA.

The present invention also includes within its scope a process for treating or preventing cancer by way of administering a therapeutically effective amount of the inventive antisense gene to a subject in need thereof.

In the inventive antisense gene therapy, the antisense gene of the present invention is administered to a subject in a conventional manner to prevent the expression of the protooncogene. For example, the antisense oligodeoxynucleotide (ODN) is mixed with a hydrophobized poly-L-lysine derivative by electrostatic interaction in accordance with the method disclosed by Kim, J. S. et al. (*J. Controlled Release* 53: 175–182, 1998) and the resulting mixed antisense ODN is administered intravenously to a subject.

The present invention also includes within its scope an anti-cancer composition comprising the antisense gene of the present invention as an active ingredient, in association with pharmaceutically acceptable carriers, excipients or other additives, if necessary. The pharmaceutical composition of the present invention is preferably formulated for administration by injection.

The amount of the antisense gene actually administered should be determined in light of various relevant factors including the condition to be treated, the chosen route of administration, the age and weight of the individual patient, and the severity of the patient's symptoms.

The protein expressed from the inventive protooncogene may be used in producing an antibody useful as a diagnostic tool. The antibody of the present invention may be prepared in the form of a monoclonal or polyclonal antibody in accordance with any of the methods well known in the art by using a protein having the amino acid sequence of SEQ ID NO: 2 or a fragment thereof. Cancer diagnosis may be carried out using any of the methods known in the art, e.g., enzyme linked immunosorbent assay (ELISA), radioimmunoassay (RIA), sandwich assay, immunohistochemical staining, western blot or immunoassay blot on polyacrylic gel, to asses whether the protein is expressed in the body fluid of the subject. Therefore, a cancer diagnostic kit containing the protein having the amino acid sequence of SEQ ID NO: 2 or a fragment thereof is also included in the scope of the present invention.

A continuously viable cancer cell line may be established by using the protooncogene of the present invention, and such a cell line may be obtained, for example, from tumor tissues formed on the back of a nude mouse by injecting fibroblast cells transformed with the protooncogene of the present invention. The cell line thus prepared may be advantageously used in searching for anti-cancer agents.

The present invention also includes within its scope a process for screening anticancer drug candidates by using said protooncogene or a fragment thereof.

The following Examples and Test Examples are given for the purpose of illustration only, and are not intended to limit the scope of the invention.

EXAMPLE 1

Yeast Two Hybrid Assay

To find a binding protein to human protooncogene KG-19 (Genebank Accession No: AF283671) protein product, yeast two hybrid assay was performed by using MATCHMAKER LexA Two-Hybrid System (Clontech Laboratories, Inc., U.S.A.) according to the previously reported procedure (Golemis, E. A., et al., *Current Protocols in Molecular Biology*, John Wiley & Sons, Inc. Chapters 20.0 and 20.1, 1996).

Cell lines and vectors used in the following experiment are listed in Catalog No. K1609-1 Kit of Clontech Laboratories, Inc.

Yeast strain EGY48 was transformed with vector p8op-lacZ and cultured in an SD/-uracil/glucose plate, a synthetic dropout medium having no uracil. The colony that grew in this plate was selected, cultured in an SD/-uracil/glucose medium, and transformed with a vector prepared by inserting KG-19 gene into the SalI and BamHI sites of vector pLexA as a 'bait plasmid'.

To examine the expression of KG-19 gene cloned in vector pLexA, western blotting using LexA antibody was performed. The result showed a 37 kDa band.

The colony expressing KG-19 gene was cultured in an SD/-uracil, -histidine/glucose medium and transformed with vector pBD42AD which is human fetal brain-derived AD (activation domain) fusion library. To confirm the binding of the bait with the library, colony lifting assay (Breeden, L. and Nasmyth, K., *Cold Spring Harbor Symposium Quant. Bio.* 50: 643–650, 1985) was performed. The interaction of the bait with the library induced the formation of a blue colony in an X-gal plate. DNA was purified from the yeast cultured using glass beads, and *E. coli* KC8 was transformed with the purified DNA by electroporation and spreading on an M9 minimal medium to select transformants. Plasmid DNA was purified from the selected transformants and transformed into *E. coli* DH5α. Then, DNA purified from the selected *E. coli* transformants was subject to HindIII digestion, to obtain a clone having 0.6 kb DNA.

EXAMPLE 2

Total cDNA Sequencing Analysis of Protooncogene KG-20

The clone obtained in Example 1 was subjected to sequencing analysis using Sequenase version 2.0 DNA Sequencing Kit (United States Biochemical, Cleveland, Ohio, U.S.A.) according to the dideoxy chain termination method. This clone was identified as a novel protooncogene consisting of 622 base pairs as described in SEQ ID NO: 1, and it was designated "KG-20". The nucleotide sequence of full-length KG-20 cDNA clone was registered at GenBank under Accession No. AF374413.

In SEQ ID NO: 1, the full open reading frame of KG-20 corresponding to base Nos. 74 to 613 is a protein encoding region and the predicted amino acid sequence derived therefrom is shown in SEQ ID NO: 2 which consists of 179 amino acids.

A λ pCEV containing the KG-20 gene was isolated from the phage λ and cut by NotI to obtain an ampicillin-resistant pCEV-LAC. pCEV-LAC was ligated by DNA ligase to obtain a recombinant vector expressing KG-20 gene. *E. coli* DH5α was transformed with the recombinant vector to obtain a transformed *E. coli* designated DH5α/KG-20/pCEV-LAC, which was deposited with Korean Collection for Type Cultures (Address: #52, Oun-dong, Yusong-ku, Taejon 305–333, Republic of Korea) on Jun. 2, 2001 under the accession number of KCTC 1028BP.

EXAMPLE 3

Northern Blot Analysis

Figure 1A:
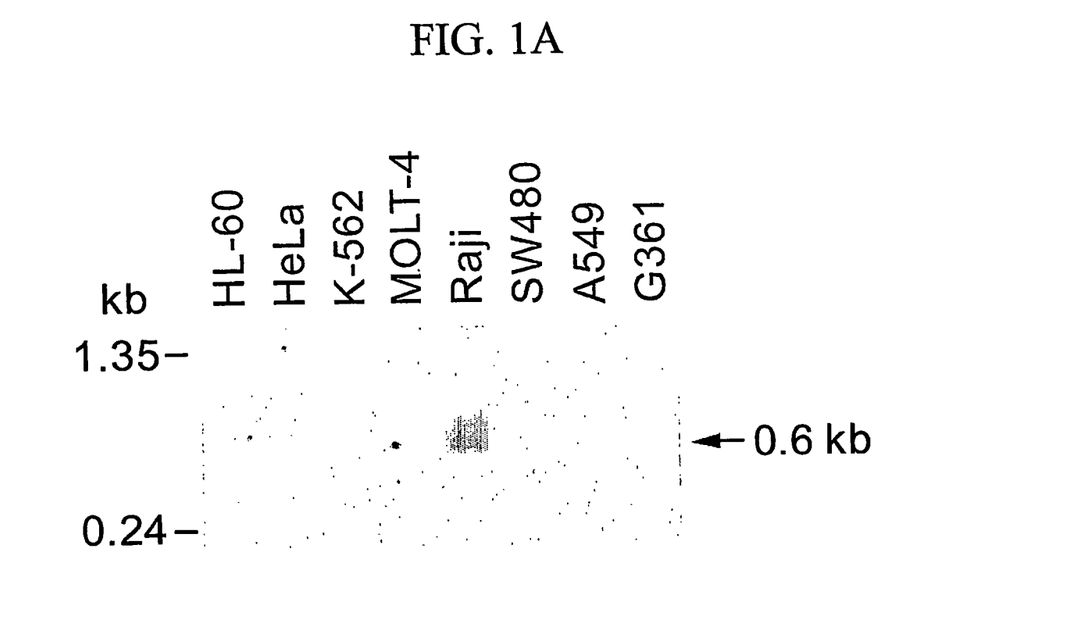
FIG. 1A: the results of northern blot analyses for protoongene KG-20 expressed in human cancer cell lines (promyelocytic leukemia HL-60 cell, HeLa cervical cancer cell, chronic myelogenous leukemia K-562 cell, lymphoblastic leukemia MOLT-4 cell, Burkitt's lymphoma Raji cell, SW480 colon cancer cell, A549 lung cancer cell and G361 melanoma cell)
Figure 1B:
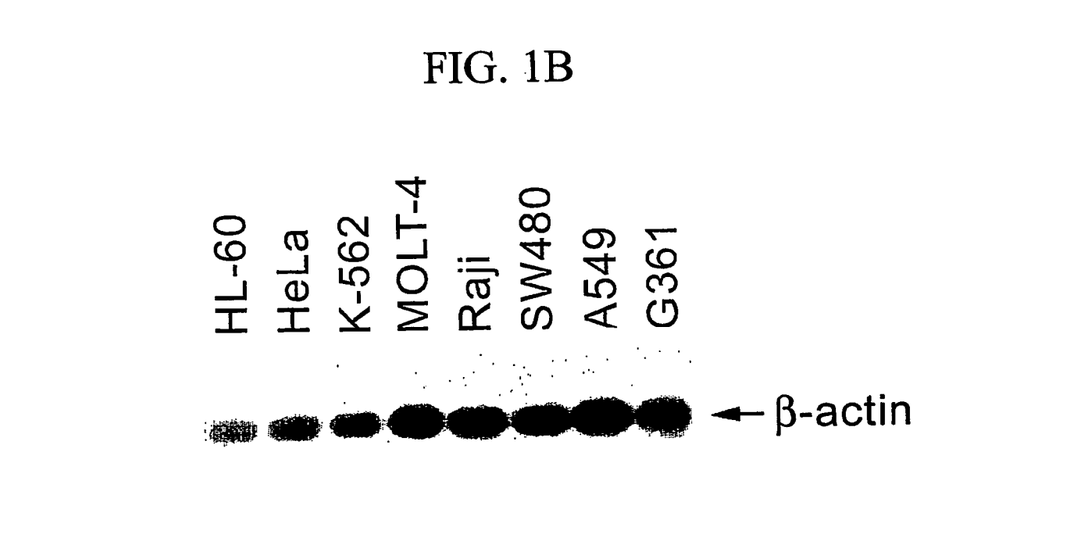
FIG. 1B: the results obtained after hybridizing the same sample of FIG. 1A with β-actin.

To determine the expression level of KG-20 gene in various tissues, northern blot analyses were also carried out as recommended by the supplier (Clontech) using a human cancer cell line sample containing purified RNAs of 8 kinds of cancer cells blotted on a nylon membrane (FIGS. 1A and 1B).

The blots were hybridized overnight at 68° C. with $^{32}$P-labeled random-primed KG-20 cDNA probe which was prepared using a Rediprime II random prime labeling system (Amersham, England). The northern blot analysis was repeated twice, and the results were quantified by densitometry. The same blots were hybridized with a β-actin probe to standardize the mRNA amount.

FIG. 1A shows the northern blot analysis for KG-20 gene expressed in human cancer cell lines, i.e., promyelocytic leukemia HL-60 cell, HeLa cervical cancer cell, chronic myelogenous leukemia K-562 cell, lymphoblastic leukemia MOLT-4 cell, Burkitt's lymphoma Raji cell, SW480 colon cancer cell, A549 lung cancer cell, and G361 melanoma cell, using KG-20 cDNA probe; and FIG. 1B, the same blot hybridized with a β-actin probe. As can be seen in FIG. 1A, the 0.6 kb transcript of KG-20 is detected at the Burkitt's lymphoma Raji, promyelocytic leukaemia HL-60, HeLa cervical cancer cell, chronic myelogenous leukaemia K-562, lymphoblastic leukaemia MOLT-4, SW480 colon cancer cell, A549 lung cancer cell, and G361 melanoma cell. Raji, in particular, shows a higher transcription level as compared with other cancer cells.

EXAMPLE 4

Construction of Expression Vectors and Transfection of Animal Cells (Step 1) Preparation of a Vector Containing KG-20

An expression vector containing the coding region of KG-20 was constructed as follows.

First, fusion vector N-terminal pFlag-CMV constructed by inserting Flag gene into an eucaryotic expression vector pcDNA3 (Invitrogen, U.S.A.) was digested with SalI/BamHI. KG-20 gene having the total coding sequence (corresponding to base Nos. 74–613 in SEQ ID NO: 1) was digested with SalI/BamHI, and the resulting SalI/BamHI fragment was inserted into the SalI/BamHI-digested N-terminal pFlag-CMV. Lipofectamine (Gibco BRL) was used to introduce the resulting vector N-terminal pFlag-CMV/KG-20 to HEK 293 epithelial cell (ACTC CRL 1753, U.S.A.), followed by selection in a medium supplemented with G418 (Gibco, U.S.A.). The resulting HEK 293 cell transfected with KG-20 was designated "KG-20 cell".

(Step 2) Human Embryonic Kidney 293 Epithelial Cell Transfected with Protooncogene KG-20

Figure 2A:
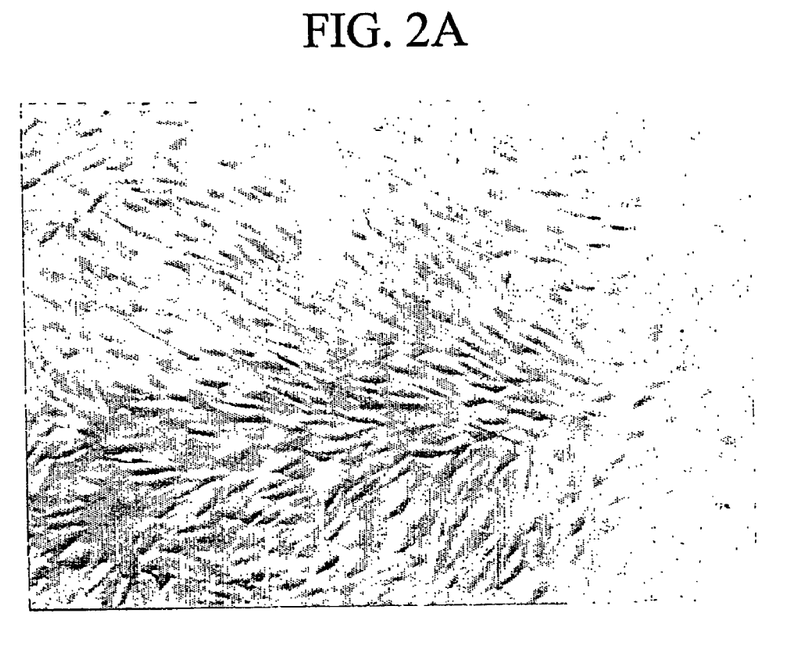
FIG. 2A: the phase-contrast feature of monolayer-cultured wild type human embryonic kidney 293 cells.
Figure 2B:
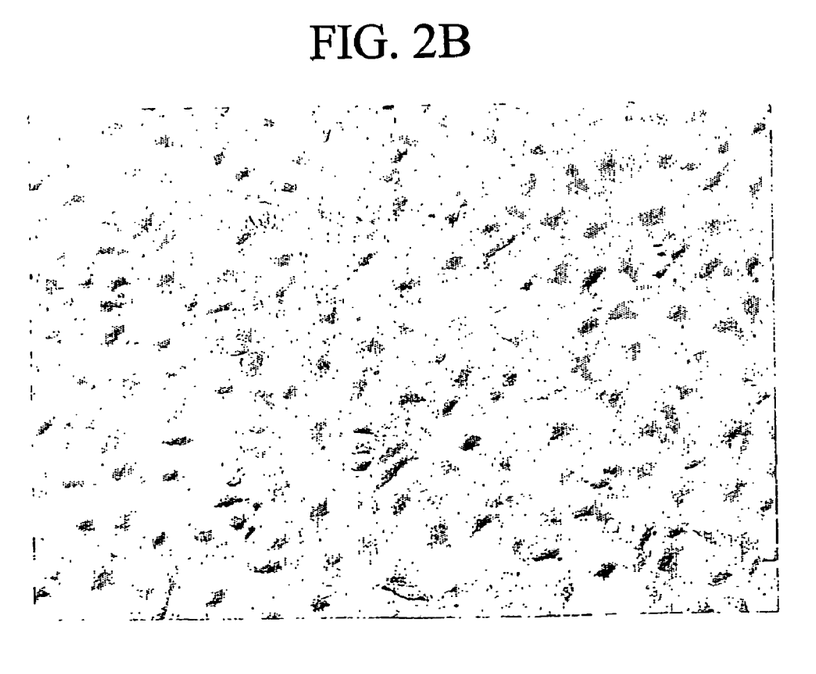
FIG. 2B: the phase-contrast feature of monolayer-cultured KG-20-transfected human embryonic kidney 293 cells.

The wild type HEK 293 cells and KG-20 cells obtained in Step 1 were each cultured in a monolayer in DMEM media containing 10% serum, and the growth features were observed with a Phase-contrast microscopy (Olympus, U.S.A.). FIGS. 2A and 2B show phase-contrast features of monolayer-cultured wild type HEK 293 cells and KG-20-transfected HEK 293 cells. As shown in FIG. 2A, the wild-type HEK 293 cells proliferated as epithelial cells, each having a spindle-shape with a long, fine nucleus and meager cytoplasm. In case of KG-20 cells, the cell shape changes into a polygonal form with an ovoid nucleus and plump cytoplasm, as shown in FIG. 2B.

Figure 3:
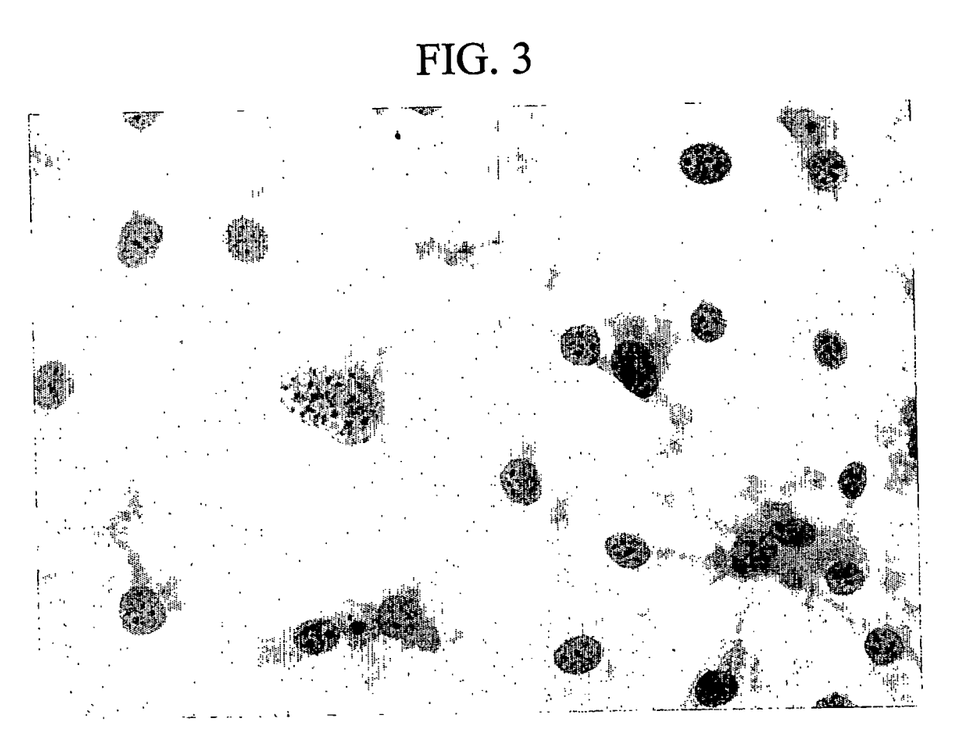
FIG. 3: hematoxylin-eosin staining of monolayer-cultured KG-20-transfected human embryonic kidney 293 cells.

Monolayer-cultured KG-20 cells stained with hematoxylin-eosin (H & E) exhibit nuclear pleiomorphism, distinct nucleoli, granular chromatin patterns, tumor giant cells and a typical mitotic figures as shown in FIG. 3.

EXAMPLE 5

Tumorigenicity of Protooncogene KG-20 in Animal

Figure 4:
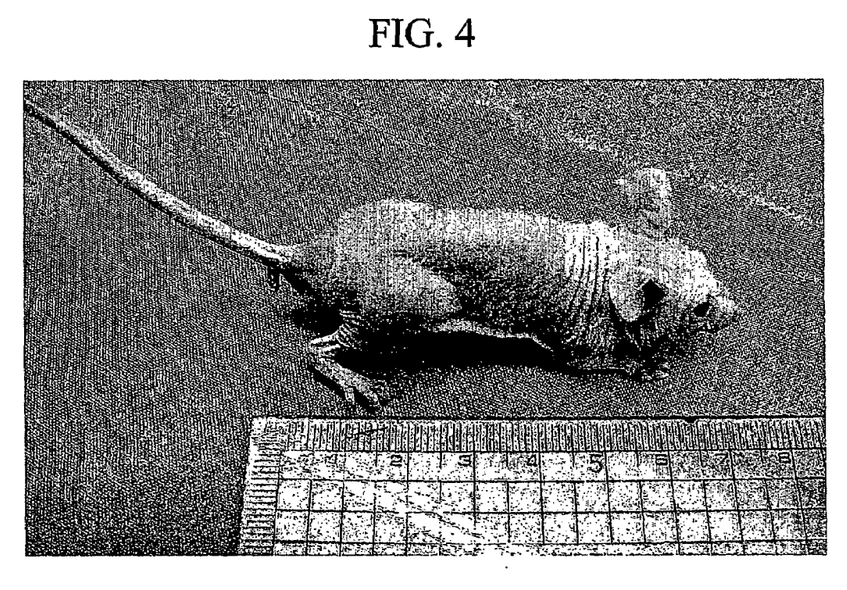
FIG. 4: tumorigenicity of KG-20 cells in nude mouse.

To analyze tumorigenicity, 5×10$^6$ KG-20 cells were injected subcutaneously into the back of 9 nude mice (5-week-old athymic nu/nu on BALB/c background). All 9 mice injected with KG-20 cells showed palpable tumors after 21 days, the tumor size becoming 2.0 cm×2.0 cm in 35 days as shown in FIG. 4.

EXAMPLE 6

Determination of Size of Protein Expressed After the Transfection of E. coli with Protooncogene KG-20

The full-length coding sequence region of protooncogene KG-20 corresponding to base Nos. 74 to 613 of SEQ ID NO: 1, which encodes amino acid Nos. 1 to 179 of SEQ ID NO: 2, was inserted into BamHI/NotI recognition site of the multiple cloning site of vector pGEX 4T-3 (Amersham Pharmacia Biotech., U.S.A.) fused with GST gene, and the resulting vector pGEX 4T-3/KG-20 was transfected into E. coli BL21 (ATCC 47092). The transfected E. coli was inoculated into an LB broth medium and cultured in a rotary shaking incubator at 37° C. for 16 hours. The culture solution was diluted with the same medium by 1/100(v/v) and incubated for 3 hours. 1 mM isopropyl β-D-thiogalactopyranoside (IPTG, Sigma) was added thereto to induce the protein synthesis.

Figure 5:
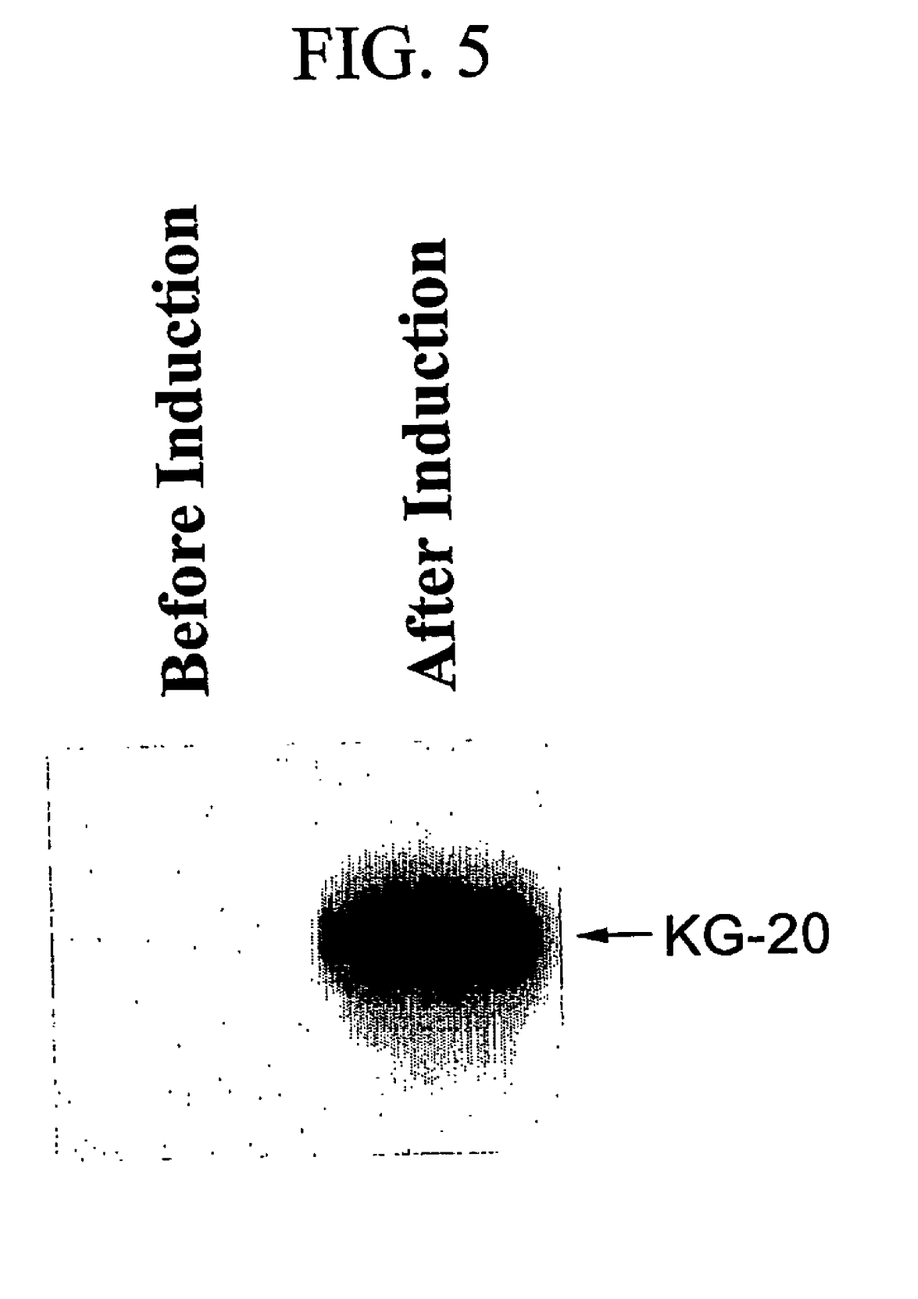
FIG. 5: sodium dodecyl sulfate (SDS)-PAGE results showing protein expression patterns before and after the IPTG induction in KG-20-transfected human embryonic kidney 293 cells.

The E. coli cells in the culture were disrupted by sonication and subjected to gel electrophoresis using 12% sodium dodecyl sulfate (SDS) before and after the IPTG induction. FIG. 5 shows the SDS-PAGE result which exhibits a protein expression pattern of the E. coli BL21 strain transfected with vector pGEX 4T-3/KG-20. After the IPTG induction, a significant protein band was observed at about 46 kDa. This 46 kDa fusion protein contained an about 26 kDa GST protein which was expressed from the gene of vector pGEX 4T-3.

While the embodiments of the subject invention have been described and illustrated, it is obvious that various changes and modifications can be made therein without departing from the spirit of the present invention which should be limited only by the scope of the appended claims.

What is claimed is:

1. A human KG-20 protooncogene consisting of the base sequence of SEQ ID NO: 1.

2. A human protooncogene consisting of a base sequence corresponding to base Nos. 74 to 613 of SEQ ID NO: 1.

3. A protein consisting of the amino acid sequence of SEQ ID NO: 2.

4. A vector comprising the protooncogene of claim 1.

5. A microorganism transformed with the vector of claim 4.

6. The microorganism of claim 5, which is *E. coli* DH5α/KG-20/pCEV-LAC (Accession No. KCTC 1028BP).

7. A process for preparing a protein having the amino acid sequence of SEQ ID NO:2 comprising culturing the microorganism of claim 5.

8. A kit for diagnosing cancer which comprises the protooncogene of claim 1.

9. A kit for diagnosing cancer which comprises the protein of claim 3.

10. A process for preparing a protein having the amino acid sequence of SEQ ID NO:2 comprising culturing the microorganism of claim 6.

11. A kit for diagnosing cancer which comprises the protooncogene of claim 2.

* * * * *